(12) United States Patent
Butterwick et al.

(10) Patent No.: US 7,955,372 B2
(45) Date of Patent: Jun. 7, 2011

(54) ENDOLUMINAL DELIVERY SYSTEM

(75) Inventors: Alexander F. Butterwick, Ann Arbor, MI (US); Ashish S. Mitra, Stanford, CA (US); Martin K. C. Ng, Sydney (AU); John W. White, San Francisco, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 1213 days.

(21) Appl. No.: 11/445,952

(22) Filed: Jun. 1, 2006

(65) Prior Publication Data
US 2007/0060998 A1 Mar. 15, 2007

Related U.S. Application Data

(60) Provisional application No. 60/686,247, filed on Jun. 1, 2005.

(51) Int. Cl.
*A61F 2/06* (2006.01)
(52) U.S. Cl. ...................................................... 623/1.11
(58) Field of Classification Search ......... 623/1.11–1.12
See application file for complete search history.

(56) References Cited

U.S. PATENT DOCUMENTS

| | | | |
|---|---|---|---|
| 5,769,882 A | 6/1998 | Fogarty et al. | |
| 5,782,789 A * | 7/1998 | Herweck et al. | 602/52 |
| 6,015,431 A | 1/2000 | Thornton et al. | |
| 6,287,315 B1 | 9/2001 | Wijeratne et al. | |
| 6,312,457 B1 | 11/2001 | DiMatteo et al. | |
| 6,334,869 B1 | 1/2002 | Leonhardt et al. | |
| 6,656,214 B1 | 12/2003 | Fogarty et al. | |
| 6,767,358 B2 | 7/2004 | Leonhardt et al. | |
| 6,852,116 B2 | 2/2005 | Leonhardt et al. | |
| 7,018,406 B2 | 3/2006 | Seguin et al. | |
| 7,044,966 B2 | 5/2006 | Svanidze et al. | |
| 2007/0225795 A1 | 9/2007 | Granada et al. | |

OTHER PUBLICATIONS

Kaplan, et al, "Histopathological effects of ethyl 2-cyanoacrylate tissue adhesive following surgical application: an experimental study," *Eur. J. Cardiothorac. Surg.*, 25(2)167.72 (2004).
Powell and Greenhalgh, "Clinical practice. Small abdominal aortic aneurysms," *N. Engl. J. Med.*, 348(19):1895-901 (2003).

\* cited by examiner

*Primary Examiner* — Todd E Manahan
*Assistant Examiner* — Eric Blatt
(74) *Attorney, Agent, or Firm* — Pabst Patent Group LLP

(57) ABSTRACT

An endoluminal delivery system is provided having an endoluminal prosthesis sized to fit through a body lumen in a first unexpanded state, where a second state is an expanded relative to the first state. At least one delivery capsule is incorporated to the outer wall of the endoluminal prosthesis, where each one of the delivery capsules has a predetermined delivery pressure. There is at least one reactant in the delivery capsule, where the endoluminal prosthesis is expanded from the first state to the second state to expand the endoluminal prosthesis against the body lumen and induce the predetermined delivery pressure to the delivery capsule, and deliver the reactants to the body lumen according to desired positioning and timing. At least one containment band incorporated to the outer wall of the endoluminal prosthesis and positioned near the delivery capsules to localize the reactants.

23 Claims, 9 Drawing Sheets

ENDOLUMINAL DELIVERY SYSTEM

CROSS-REFERENCE TO RELATED APPLICATIONS

This application is cross-referenced to and claims the benefit from U.S. Provisional Patent Application Ser. No. 60/686,247 filed Jun. 1, 2005, which is hereby incorporated by reference.

FIELD OF THE INVENTION

The invention relates generally to endoluminal prosthetics. More particularly, the invention relates to providing substances to endoluminal prosthesis grafts

BACKGROUND

The lumen is the interior of a vessel within the body, such as the small central space in an artery or vein, or any of their relating vessels, down which blood flows. An aneurysm is a localized dilation of an artery that eventually becomes larger and ruptures. Most aneurysms occur in the main artery of the body such as Abdominal Aortic Aneurysms (AAAs) or Thoracic Aortic Aneurysms (TAAs). AAA is a common disease that is associated with significant mortality if left untreated. A limiting factor to open repair is the patient's physiological suitability to survive the procedure with acceptable risks. While low morbidity and mortality with open AAA repair is reported, patients with associated comorbidities such as cardiovascular or pulmonary conditions may be at an increased risk with surgical repair. The need to better serve these high-risk patients led to the development of endovascular approaches to treat AAA. Endovascular AAA repair involves minimally invasive, transfemoral delivery of a covered stent within the aneurysm, thereby effectively excluding the aneurysm from circulation.

Many patients for whom endovascular AAA repair could potentially be of benefit do not qualify because of anatomic considerations. The primary anatomic reason for exclusion is the presence of a short proximal neck length. A neck length of 15 mm or greater has been considered essential for proper fixation and sealing for stent-grafts. Currently, the vast majority of patients with short neck AAAs are treated by surgical repair.

Thoracic aneurysms may occur in the ascending aorta, the aortic arch, or the descending thoracic aorta. Descending TAA are much easier to access and treat than other manifestations of the disease. Many of the characteristics that are common in AAA are also present in TAA. The cumulative risk of rupturing a TAA is related to aneurysm diameter. The treatment of descending TAA is an ongoing study. According to one study, the placement of endoluminal stent-grafts to exclude the dissected or ruptured site of thoracic aortic aneurysms is a technically feasible and relatively safe procedure.

The replacement aortic valve needs to be secured at the root of the aorta, across the annulus of the existing valve. The typical annulus diameter can exhibit many of the same characteristics as an aorta with an aneurysm (anatomic variability, calcification, presence of diseased tissue). Like AAA stent-grafting, both fixation and seal are essential in aortic valve replacement surgery Migration and leakage of a stent-graft after apparently successful endovascular repair raises concerns about the long-term durability of endovascular repair. Leaks from fabric tears or between modular systems that permit continued and expansion of the aneurysmal sac can also lead to rupture. The occurrence of migration or leakage requires re-intervention, mostly by insertion of a proximal extender cuff. Endoleaks may persist in 10-15% of patients while late endoleaks may develop in another 5-10% of patients.

A need for delivery of endoluminal reactants has proved to be a vital step in successfully addressing endoleaks and stent migration has generated much activity in solving these issues.

Recent attempts in resolving stent-graft migration and fixation issues have emerged in various forms. In one attempt a graft apparatus further has a plurality of light degradable polymer outer packets containing a tissue adhesive, which is released by fiber-optic scope after the graft is implanted. Expandable foam cuffs surround the middle portion of the graft to promote clotting within the aneurysm sac. The drawbacks to this effort are in a lack of control of the adhesive release, where the light degradable polymer packets are dependent on the light intensity and the light sours proximity to the packets. Further, in situations with high numbers of packets, the release time may become very lengthy.

In another attempt, a self-expandable stent in the form of wires used anchors, including barbs, hooks, or pins were used as a fixation device. However, this effort left unresolved the sealing of the device.

In another attempt, a sealing layer conforms to the interface region between the outer wall of the tubular prosthesis and the inner wall of the body lumen. The sealing layer expanded in situ in order to conform to the geometry of the interface region. The material was partially hardened after introduction to the target location within the body lumen and in situ expansion of the tubular prosthesis body. This device has limits in providing reactants to the body lumen.

In another effort, a sealing element was secured to the outer surface of a tubular member. The tubular member was expandable to engage an endolumenal wall. The sealing element occluded flow around the tubular member between the outer surface and the endolumenal wall. Anchors were used to secure the tubular member to the endolumenal wall, as the seal member was positioned to protect against flow through leakage paths formed at localized areas of deformation in the tubular wall adjacent to the anchors. This device has limits in providing reactants to the body lumen.

In all these attempts, a need still exists to deliver a variety of reactants to an endoluminal prosthesis independently or simultaneously according to precise timing and positioning. Additionally, the need further requires a device that is flexible enough to conform to the many different anatomical presentations of AAAs, TAAs & the aortic valve annulus. A desirable device must be fixed to the wall of the aorta or aortic valve annulus after the physician has found the optimal location for the device, where fixation after location is a key aspect. Such a device must fully seal the proximal end of the graft to prevent endoleaks and perivalvular leaks, and achieve a degree of fixation that will prevent subsequent device migration or dislodgement. Accordingly, there is a need to develop an endoluminal delivery system to overcome the current shortcomings in the art.

SUMMARY OF THE INVENTION

The present invention provides an endoluminal delivery system, having an endoluminal prosthesis with a first state and a second state. The endoluminal prosthesis is sized to fit through a body lumen in the first state, where the second state is expanded relative to the first state. At least one delivery capsule is incorporated to the outer wall of the endoluminal prosthesis, where each one of the delivery capsules has a predetermined delivery pressure. There is at least one reactant in the delivery capsule, where the endoluminal prosthesis is expanded from the first state to the second state to expand the endoluminal prosthesis against the body lumen and induce the predetermined delivery pressure to the delivery capsule, according to desired positioning and timing, to deliver the reactant to the body lumen.

Further, in one embodiment to the invention, the endoluminal delivery system has at least one containment band incorporated to the outer wall of the endoluminal prosthesis and is positioned near the delivery capsules to localize the reactants. In another embodiment of the invention, the containment band has a non-permeable layer on the outer surface, the inner surface, or both the outer surface and the inner surface. In another embodiment of the invention, the containment band is an absorbent material to absorb the reactants and receive tissue growth into the material. In another embodiment of the invention, the containment band envelopes the delivery capsules. In another yet embodiment of the invention, the containment band has a span exposing a region of the delivery capsules.

The body lumen, according to other embodiments of the invention, may be one or more of cardiac chambers, cardiac appendages, cardiac walls, cardiac valves, arteries, veins, nasal passages, sinuses, trachea, bronchi, oral cavity, esophagus, small intestine, large intestine, anus, ureters, bladder, urethra, vagina, uterus, fallopian tubes, or auditory canals.

The reactant in the delivery capsules, according to another embodiment of the invention, is at least an adhesive fluid, or at least a tissue growth promoting fluid, or at least an adhesive fluid and a tissue growth promoting fluid. The reactant may be one or more of cyanoacrylate esters, 2-octylcyanoacrylate, n-butyl cyanoacrylate, albumin based sealants, hydrogel sealants, copolymer of polyethylene glycol with acrylate end caps, polyethylene glycol, polylactic acid, fibrin glue, polymethylmethacrylate, photo-activated glue, vascular endothelial growth factor, fibroblast growth factor, adenoviral vectors, or small interference RNA.

According to another embodiment of the invention, the delivery capsules may have a plurality of predetermined release pressures. In a further embodiment of the invention, the delivery capsules are arranged in a pattern according to release pressures, or arranged according to reactant, or arranged according to delivery pressures and according to reactant to release the reactant when subject to the predetermined pressures. Further the delivery capsules may be arranged in a noninterference pattern, wherein the delivery capsules do not interfere with each other when in the first state or in said the state.

In other embodiments of the invention, the delivery capsules environ the endoluminal prosthesis, the delivery capsules may contain or appose a delivery capsule puncture barb, the delivery capsules may have an exit aperture, the delivery capsules may be perforated, the delivery capsules further comprise an impermeable backing barrier or an absorbent base, or the delivery capsule have an inelastic element on the delivery capsule to breach the delivery capsule when the endoluminal prosthesis expands to the second state. In yet another embodiment of the invention, the delivery capsules release a first volume of the reactant when subject to a first pressure and release a second volume of the reactant when subject to a second pressure.

In another embodiment of the invention, the endoluminal prosthesis is sized to fit through a stent and sized to fit through the body lumen and then bridge a stent migration gap from the stent to the body lumen. A stent migration gap occurs after a previously deployed stent migrates distally from its initial fixation point. The migration gap is defined as the space between the original fixation point and the distal opening of the previously implanted device. In the current vocabulary, these devices are called "cuffs." In another embodiment of the invention the endoluminal prosthesis is a shape memory or superelastic alloy held by a sheath in the first state. In another embodiment of the invention, the endoluminal prosthesis has the delivery capsules juxtaposed in a generally tube shape.

A method of using an endoluminal delivery system, according to one embodiment of the invention, includes the steps of providing a body lumen, inserting an endoluminal delivery system to the body lumen, wherein the endoluminal delivery system holds at least one delivery capsule having predetermined release pressure, and having at least one reactant in the delivery capsule, inserting an expandable balloon to the endoluminal delivery system, and pressurizing the expandable balloon to a predetermined pressure to expand the expandable endoluminal delivery system and induce the predetermined pressure to the delivery capsule against the body lumen to release a predetermined volume of the reactant according to desired positioning and timing that is localized to deliver the reactant to the body lumen.

In another embodiment of the invention, the endoluminal delivery system is an endoluminal prosthesis inserted to a body lumen, at least one delivery capsule having predetermined release pressure incorporated to the endoluminal prosthesis, and at least one reactant in said delivery capsule.

The current invention specifically describes a spatially and temporally accurate pressure-regulated endoluminal delivery system which may be used for a variety of substances including adhesives, a sealing substance, drugs, biologic agents, gene-delivery agents and/or gene-targeting molecules.

While the invention may be applied in a variety of medical scenarios, it has been conceived, primarily, as an endovascular fixation mechanism to enable percutaneous fixation and seal of large endovascular devices such as an abdominal aortic aneurysm endograft.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Figure 1:
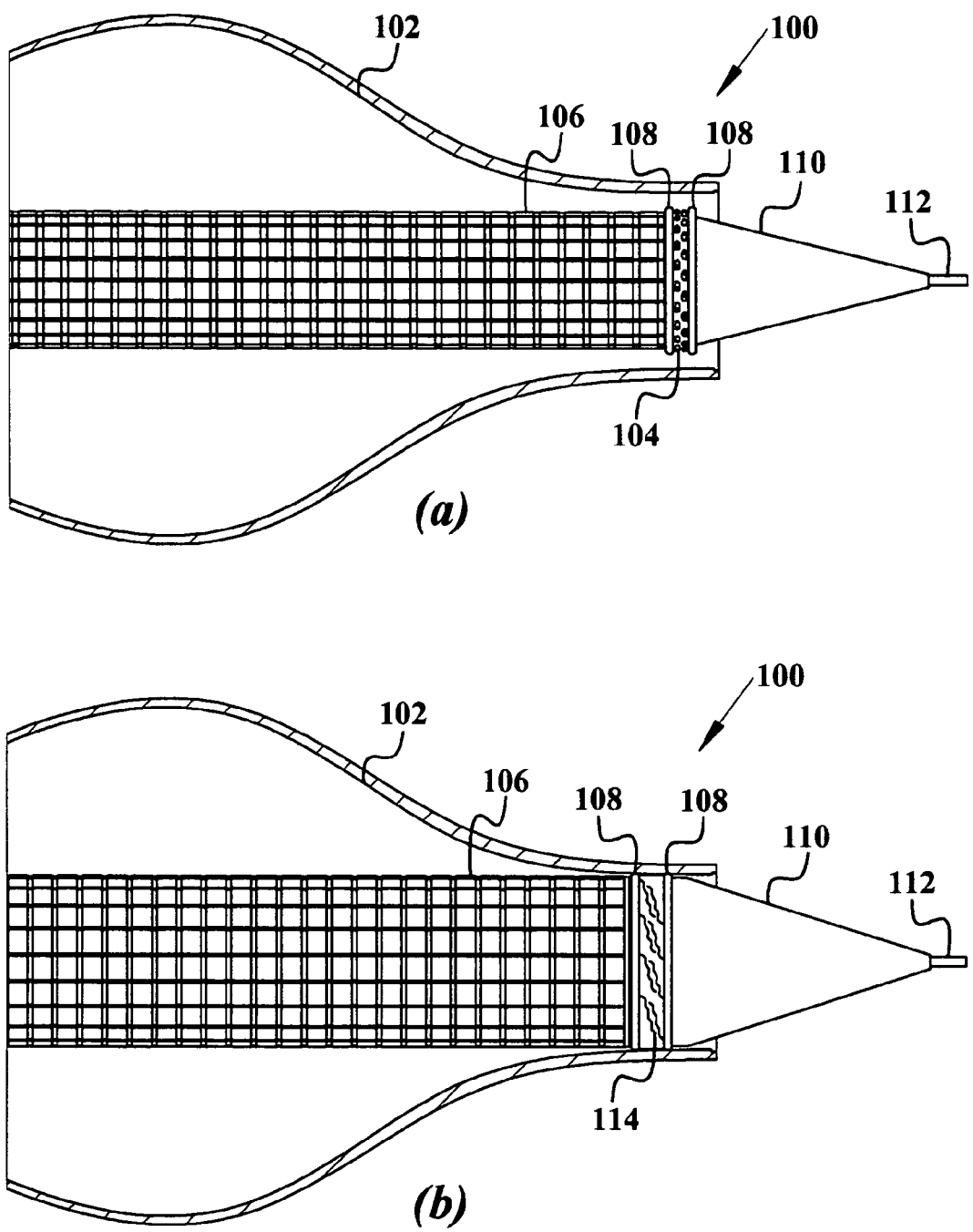
FIGS. 1a-b depict planar, partial-cutaway views of an endoluminal delivery system according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention is an endoluminal delivery system that addresses endovascular treatment of Abdominal Aortic Aneurysms (AAAs), or Thoracic Aortic Aneurysms (TAAs) and resolves problems such as device migration and endoleaks. This system also addresses cardiac valve disease and resolves leakage and migration in the context of percutaneously implanted cardiac valves. The endoluminal delivery system conforms to many different anatomical presentations of AAAs, TAAs and the cardiac valve annuli. The endoluminal delivery system is fixed to the wall of the aorta or cardiac valve annuli after the physician has found the optimal location for the device to enable fixation after location. The endoluminal delivery system fully seals the proximal end or distal end of the graft to prevent endoleaks and perivalvular leaks, and prevents subsequent device migration or dislodgement, while delivering other critical reactants to the localized region.

The endoluminal delivery system has one or more capsules located on an endoluminal prosthesis (e.g. aortic stent-graft, percutaneous heart valve or left atrial appendage closure device). The capsules enclose the reactants to be delivered which may include adhesives, a sealing substance, drugs, biologic agents, gene-delivery agents, and gene-targeting molecules. More specifically the capsules may include cyanoacrylate esters, 2-octylcyanoacrylate, n-butyl cyanoacrylate, albumin based sealants, hydrogel sealants, copolymer of polyethylene glycol with acrylate end caps, polyethylene glycol, polylactic acid, polymethylmethacrylate, photo-activated glue, vascular endothelial growth factor, fibroblast growth factor, adenoviral vectors, or small interference RNA.

Reactants are released from the capsules by application of pressure such as by balloon inflation, for example. A matrix material to absorb and/or spatially regulate release of the reactantss to be delivered is located within a predetermined proximity of the capsules. The matrix may facilitate endoluminal conformability and apposition of the prosthesis, as well as stimulate selective tissue ingrowth into the matrix. It further prevents embolization of reactants distally in the body during or after release.

The endoluminal delivery system may be used for achieving fixation and seal of tubular grafts or other implantable devices for endoluminal placement within a body lumen, including blood vessels or other vascular spaces. The method of defining adhesion area is not limited to just the use of capsules. Others include semi-permeable membrane, microfluidic channels filled with biologics from either outside the stent or from a capsule within the stent, electronic control of capsules for controlled release of biologics, or control of polymerization through selective application to light for photosensitive glues. Different embodiments of the endoluminal delivery system include use of the tube to which the endoluminal delivery system is attached, where the tube has a capsule delivery system attached to the proximal and distal ends. The interior of the tube may function as a conduit for blood, contain further prostheses (such as but not limited to heart valves, valves to control the direction of flow, drug delivery devices, stents or coated stents, or volume fillers), or be connected to other biologic tissue (such as but not limited to bowel, blood vessel, esophageal tissue or bronchial tissue). The tube may consist of a material (such as but not limited to polyurethane, polyethylene teraphthalate (including Dacron), polytetrafluoroethylene, natural biologic polymer, such as collagen, vascular tissue, fibrin film, or any other suitable graft material) that will provide a conduit for biologic fluids, food or air. The tube may contain a special, resistant backing (such as but not limited to flexible plastic, rubber) which would prevent material within the capsule from migrating back into the tube. In this embodiment, at least one capsule, which releases at a predetermined pressure above the blood pressure commonly found in the human vasculature system, or upon contact with water or blood, or after a certain amount of time elapses after contact with blood, or due to exposure to a particular energy source (such as but not limited to electromagnetic energy, electromagnetic radiation, heat, DC current, RF energy), or is released by a chemical. The capsules may be arranged as a single circumferential capsule around the proximal or distal ends of the tube, or multiple capsules arranged circumferentially around the proximal or distal ends of the tube. These multiple capsules may be arranged in a single circumferential line or may be arranged in multiple circumferential lines. These lines may be parallel to each other, off-set (so that they overlap), staggered, or parallel but at an angle. The capsules may be any shape, such as a semi-spherical shape. The capsules may be constructed of even amounts of material, could be of varied thickness, or may be treated in such a way as to preferentially rupture in one location after application of rupturing mechanism. Treatments may include scoring or weakening of the capsule in specific locations. Capsules may rupture due to mechanical assistance. Barbs or hooks may be located inside or apposed to the exterior of the capsules and may pierce the capslule wall upon application of pressure due to external force or device expansion. Tabs of non-expansive material could also be attached to the surface of the reservoir and cause rupture upon application of pressure due to external force or device expansion. The reactant may be delivered through the walls of the capsule, which may be semi-permeable. The reactant may be delivered from a capsule through micro-machined channels to the area of interest. The reactant may slowly diffuse outward through the walls of the tube due to diffusion properties.

A matrix may be arrayed circumferentially proximally, distally or both relative to the capsules. The matrix may completely cover the capsules, partially cover the capsules, or contain capsules impregnated within the matrix itself. The matrix may be constructed of shape memory materials, which may hold their shape indefinitely upon application of pressure. The matrix may be constructed of a material that will continually reshape itself as the body surface to which it is connected remodels or moves. The matrix may contain a non-permeable membrane at the edge furthest from the capsules. The matrix may be impregnated with an adhesive (such as but not limited to cyanoacrylate esters, 2-octylcyanoacrylate, n-butal cyanoacrylate, albumin based sealants, hydrogel sealants—eosin based primer consisting of a copolymer of polyethylene glycol with acrylate end caps and a sealant consisting of polyethylene glycol and polylactic acid, fibrin glue, polymethylmethacrylate), a sealing substance, drugs, biologic agents (e.g. vascular endothelial growth factor, fibroblast growth factor etc,), gene-delivery agents (e.g. adenoviral vectors etc.) and/or gene-targeting molecules (e.g. small interference RNA) that is released only after application of a predetermined pressure above the blood pressure commonly found in the human vasculature system, upon contact with water or blood, after a certain amount of time elapses after contact with blood, due to exposure to a particular energy source (such as but not limited to electromagnetic radiation, heat, DC current, RF energy) or a chemical.

Some methods of using the endoluminal delivery system may include delivery to the area of interest through a body lumen (such as but not limited to the arterial system, venous system, esophagus, respiratory tract, gastro-intestinal tract) or through a surgical incision. The endoluminal delivery system may be guided either over a wire to the location that is of interest or by direct visualization. The endoluminal delivery system may be collapsed to enable delivery through smaller diameter spaces. The endoluminal delivery system is changed from its collapsed form by a self-expanding material either embedded in the endoluminal delivery system or attached to the tube, pressure due to a balloon system, or electromechanically. More specifically, the expansion may be engaged by removing an outer tube, or sheath, that encloses a self-expanding device. The endoluminal delivery system may be located in the correct anatomical position and continually adjusted before the reactants are delivered. Delivery of the reactant may be affected by a device that is part of the original endoluminal delivery system (such as an electromechanical device or tabs that are removed by human force), or by a second device also inserted either through a body lumen (such as but not limited to the arterial system, venous system, esophagus, respiratory tract, gastro-intestinal tract) or through a surgical incision. A second device used to release the reactant might include a balloon to induce super-physiologic pressure; an energy-emitting balloon, catheter, or fiber; or an expanding metal object to provide external pressure.

Referring now to the drawings, FIGS. 1a-1b depict planar, partial-cutaway views of an endoluminal delivery system 100 according to one embodiment of the invention. Shown is the endoluminal delivery system 100 that has an endoluminal prosthesis 106 having a first state and a second state. The endoluminal prosthesis 106 is sized to fit through a body lumen 102 in the first state, and the second state of the endoluminal prosthesis 106 is expanded relative to said first state. At least one delivery capsule 104, is incorporated to the outer wall of the endoluminal prosthesis 106 wherein each one of the delivery capsules 104 has a predetermined delivery pressure for rupture or permeation. At least one reactant 114 is in the delivery capsule. The endoluminal prosthesis 106 is expanded from the first state to the second state to expand the endoluminal prosthesis 106, and thus the delivery capsules 104, against the body lumen 102 and induce the predetermined delivery pressure to the delivery capsules 104 according to desired positioning and timing to deliver the reactants 114 to the body lumen 102.

Shown in FIG. 1a is the endoluminal delivery system 100, according to one embodiment of the invention, positioned in a body lumen 102 in a first, unexpanded state, with delivery capsules 104 integrated to the endoluminal prosthesis 106, and with containment bands 108 for localizing the delivered reactant 114 integrated to the endoluminal prosthesis 106 near the delivery capsules 104, where shown are a pair of containment bands 108 on each side of the group of delivery capsules 104. A balloon 110 while in the first unexpanded state is depicted inserted to the endoluminal prosthesis 106 to allow desired positioning of the endoluminal delivery system 100 with the aid of a guide wire 112. The body lumen 102 may be selected from a group consisting of cardiac chambers, cardiac valves, arteries, veins, nasal passages, sinuses, trachea, bronchi, oral cavity, esophagus, small intestine, large intestine, anus, ureters, bladder, urethra, vagina, uterus, fallopian tubes, or auditory canals.

Shown in FIG. 1b is the endoluminal delivery system 100 in a second expanded state, with the delivery capsules 104 (not shown) expanded against the body lumen 102 to a predetermined pressure releasing the reactant 114. The reactant 114 in the delivery capsules 104 may be at least an adhesive fluid, or at least a tissue growth promoting fluid, or at least an adhesive fluid and a tissue growth promoting fluid. Further, the reactant 114 may be selected from cyanoacrylates (including 2-octyl cyanoacrylate, n-butyl cyanoacrylate, iso-butyl-cyanoacrylate and methyl-2- and ethyl-2-cyanoacrylate), albumin based sealants, fibrin glues, resorcinol-formaldehyde glues (e.g. gelatin-resorcinol-formaldehyde), ultraviolet-(UV) light-curable glues (e.g. styrene-derivatized (styrenated) gelatin, poly(ethylene glycol) diacrylate (PEGDA), carboxylated camphorquinone in phosphate-buffered saline (PBS), hydrogel sealants—eosin based primer consisting of a copolymer of polyethylene glycol with acrylate end caps and a sealant consisting of polyethylene glycol and polylactic acid, collagen-based glues and polymethylmethacrylate, vascular endothelial growth factor, fibroblast growth factor, hepatocyte growth factor, connective tissue growth factor, placenta-derived growth factor, angiopoietin-1 or granulocyte-macrophage colony-stimulating factor. Other reactants 114 may include agents modulating cellular behavior in relation to bioprosthesis, such as microfibrillar collagen, fibronectin, fibrin gels, synthetic Arg-Gly-Asp (RGD) adhesion peptides, tenascin-C, Del-1, CCN family (e.g. Cyr61) hypoxia-inducible factor-1, acetyl choline receptor agonists and monocyte chemoattractant proteins. Further reactants 114 may include Gene delivery agents such as viral vectors for gene delivery (adenoviruses, retroviruses, lentiviruses, adeno-associated viruses) and non-viral gene delivery agents/methods (e.g. polycation polyethylene imine, functional polycations, consisting of cationic polymers with cyclodextrin rings or DNA within crosslinked hydrogel microparticles etc.). Still further reactants 114 could include agents modulating cell replication/proliferation, such as target of rapamycin (TOR) inhibitors (including sirolimus, everolimus and ABT-578), paclitaxel and antineoplastic agents (including alkylating agents (e.g. cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase), antimitotic agents (vincristine, vinblastine, vinorelbine, docetaxel, estramustine) and molecularly targeted agents (imatinib, tretinoin, bexarotene, bevacizumab, gemtuzumab ogomicin and denileukin diftitox)). Additionally, the reactants 114 may be steroids such as corticosteroids, estrogens, androgens, progestogens and adrenal androgens. Still further reactants 114 may include antiplatelet, antithrombotic and fibrinolytic agents agents such as glycoprotein IIb/IIIa inhibitors, direct thrombin inhibitors, heparins, low molecular weight heparins, platelet adenosine diphosphate (ADP) receptor inhibitors, fibrinolytic agents (streptokinase, urokinase, recombinant tissue plasminogen activator, reteplase and tenecteplase etc). Additionally, gene targeting molecules such as small interference RNA, mico RNAs, DNAzymes and antisense oliogonucleotides, or cells such as progenitor cells (endothelial progenitor cells, CD34+ or CD133+ monocytes, hemopoietic stem cells, mesemchymal stem cells, embryonic stem cells) and differentiated cells (endothelial cells, fibroblasts and smooth muscle cells) may be included reactants 114. Finally, Drug delivery agents like mucoadhesive polymers (e.g. thiolated polymers), or pharmacologic agents of local treatment of atherosclerosis such as high density lipoprotein cholesterol (HDL), HDL mimetics and hydroxymethylglutaryl CoA (HMG-CoA) reductase inhibitors may be included reactants 114.

Figure 2:
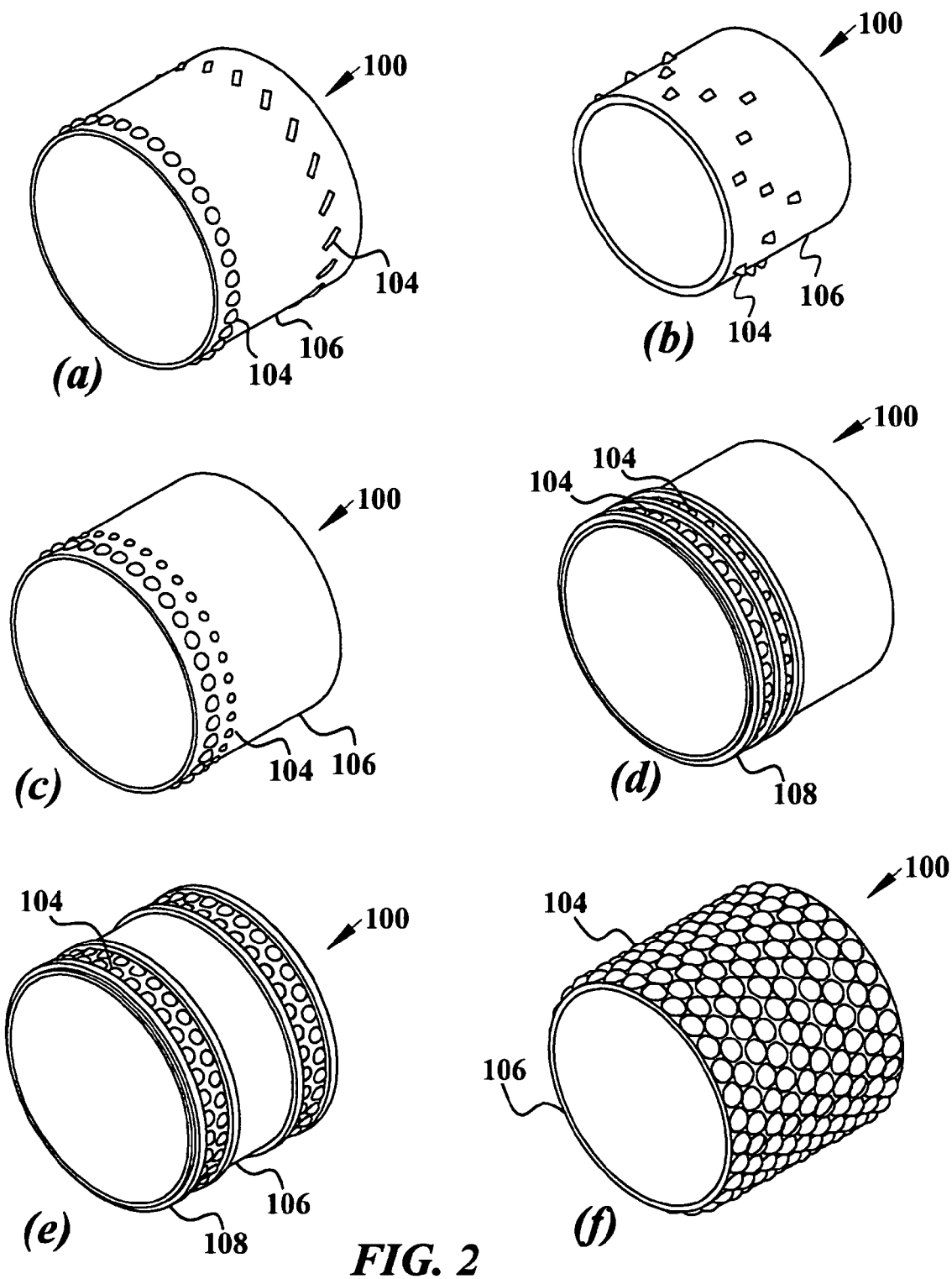
FIGS. 2a-2f show perspective view of different embodiments according to the present invention.

FIGS. 2a-2f depict perspective views of some exemplary embodiments of the current invention. FIG. 2a depicts an endoluminal delivery system 100 in an unexpanded state with delivery capsules 104 incorporated in two configurations along the outer wall of the endoluminal prosthesis 106B, where one configuration is in a series to form a ring pattern and another configuration depicts a diagonal orientation of elongated delivery capsule 104 according to one embodiment of the current invention. FIG. 2b depicts an endoluminal delivery system 100 in an unexpanded state with delivery capsules 104 incorporated along the outer wall of the endoluminal prosthesis 106 in a staggered pattern according to one embodiment of the current invention, where the delivery capsules 104 may be arranged according to predetermined release pressures, or according to reactant 114, or according to the reactant 114 and release pressure to release the reactant 114 when subject to predetermined pressures. Further depicted in FIG. 2b are delivery capsules 104 in a generally polygon shape, where it is understood that the delivery capsules 104 may take on many other shapes and geometries without departing from the spirit of the invention. FIG. 2c depicts an endoluminal delivery system 100 in an unexpanded state with delivery capsules 104 incorporated along the outer wall of the endoluminal prosthesis 106 in two series offset from one another to form a parallel ring pattern according to one embodiment of the current invention, where the delivery capsules 104 may be arranged according to predetermined release pressures to release the reactant 114 when subject to predetermined pressures.

The endoluminal delivery system 100 has at least one containment band 108 incorporated to the outer wall of the endoluminal prosthesis 100 and positioned near the delivery capsules 104 to localize the reactant 114. The containment band 108 may have a non-permeable layer (not shown) on an outer surface, or on an inner surface, or an outer surface and an inner surface. The containment band 108 may further have absorbent material to absorb the reactants 114 and receive tissue growth therein (not shown). FIG. 2d depicts an endoluminal delivery system 100 in an unexpanded state with delivery capsules 104 incorporated with the endoluminal prosthesis 106 and arranged according to the release pressure, or according to reactant 114, or according to the reactant 114 and release pressure. Further depicted are containment bands 108 near the patterns of delivery capsules 104 for localizing the reactants 114 or promoting tissue growth therein, or for localizing the reactants 114 and promoting tissue growth therein. The containment bands 108 may additionally regulate the movement of the reactant 114 along the outer surface of the endoluminal prosthesis 106, where the containment band 108 may be made of permeable, semi-permeable, or impermeable material. According to other embodiments of the current invention, the containment bands 108 may be generally ring-shape with an inner surface, an outer surface, a proximal wall and a distal wall, where any of the surfaces or walls may be made of permeable, semi-permeable, or impermeable material. Further the containment band 108 could be in the shape of a sine wave around the top of the device (not shown).

The endoluminal delivery system 100 according to one embodiment, has an endoluminal prosthesis 100 sized to fit through a stent and sized to fit through said body lumen whereby bridging a stent migration gap from the stent to the body lumen 102. A stent migration gap occurs after a previously deployed stent migrates distally from its initial fixation point. The migration gap is defined as the space between the original fixation point and the distal opening of the previously implanted device. In the current vocabulary, these devices are called "cuffs." FIG. 2e depicts an endoluminal delivery system 100 in an unexpanded state with delivery capsules 104 and containment bands 108 incorporated along the outer wall of the endoluminal prosthesis 106 located at the proximal and distal ends of the endoluminal prosthesis 106, as one example of the endoluminal delivery system 100 for use with a stent migration gap. Shown are the delivery capsules 104 in parallel ring patterns and arranged according to the release pressure, or according to reactant 114, or according to the reactant 114 and release pressure, and a plurality of containment bands 108 for localizing the reactants 114 or promoting tissue growth therein, or for localizing the reactants 114 and promoting tissue growth therein.

FIG. 2f depicts an endoluminal delivery system 100 in an unexpanded state with delivery capsules 104 incorporated along the outer wall of the endoluminal prosthesis 106 and arranged in a noninterference pattern, where the delivery capsules 104 do not interfere with each other when in a first state or in a second state. Shown is the endoluminal delivery system 100 according to one embodiment, with the delivery capsules 104 juxtaposed in a generally tube shape, where shown the delivery capsules 104 arranged in a collapsed, first state without interfering with one another.

In another embodiment of the invention, the endoluminal prosthesis 106 of FIGS. 2a-2e may be of any length, diameter or generally tubular shape without departing from the spirit of the invention.

Figure 3:
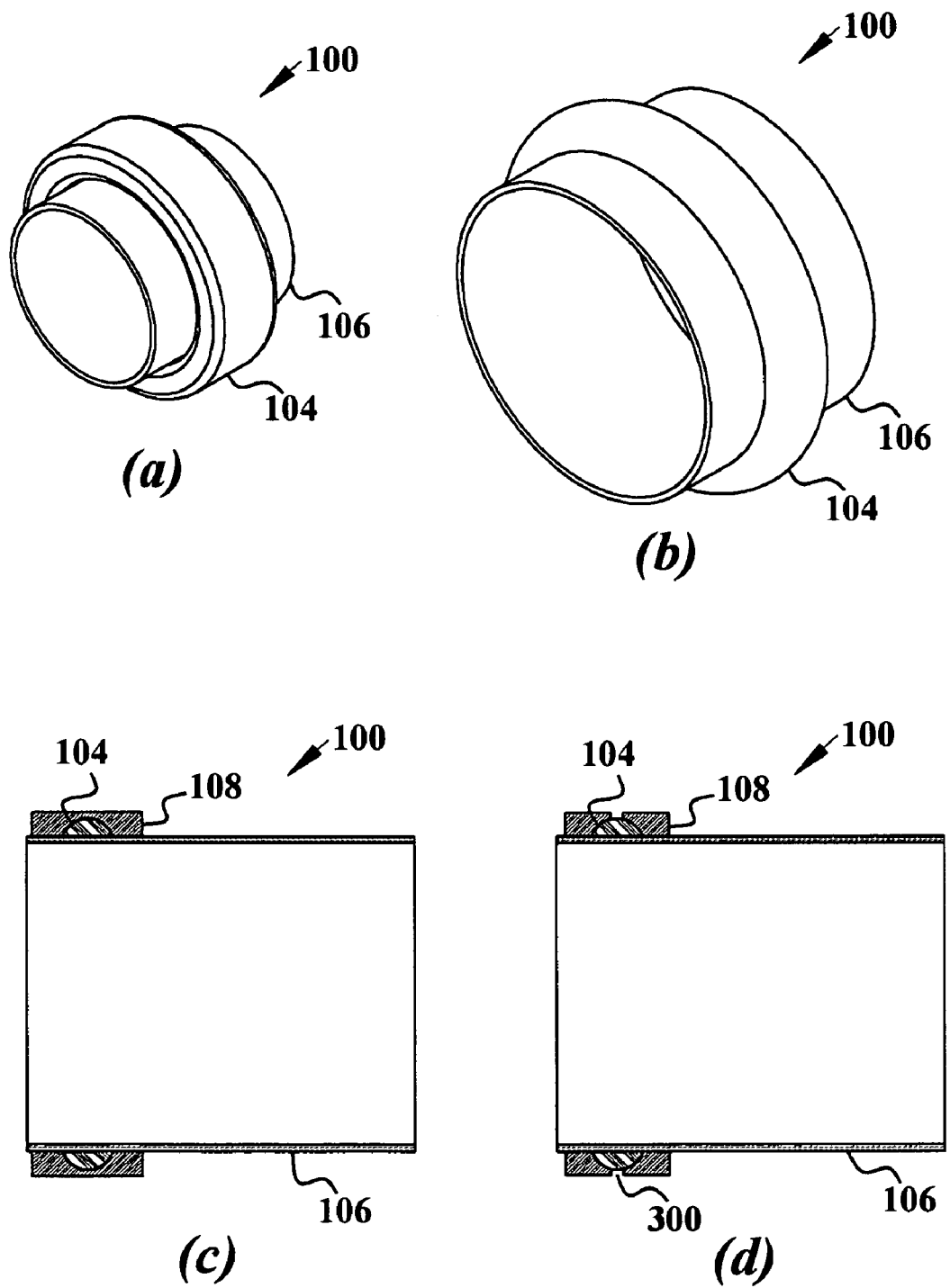
FIGS. 3a-3d depict delivery capsule and containment band relations according to the present invention.

In another embodiment the endoluminal delivery system 100 has a containment band 108 the envelopes a single delivery capsule 104, where the delivery capsule 104 is generally annulus-shape, incorporated to environ the endoluminal prosthesis 106. FIGS. 3a-3b depict perspective views of a single delivery capsule 104 around the endoluminal prosthesis 106. FIG. 3a depicts one embodiment of the endoluminal delivery system 100 with the endoluminal prosthesis 106 in the first (unexpanded) state having a delivery capsule 104, also in an unexpanded state, with a predetermined volume for holding the reactant 114 (not shown). FIG. 3b depicts the endoluminal delivery system 100 with the endoluminal prosthesis 106 in the second (expanded) state relative to the state depicted in FIG. 3a having the delivery capsule 104 also in the expanded state, where the delivery capsule 104 has expanded from a first shape to a second shape.

FIGS. 3c-3d depict planar cutaway views of the endoluminal delivery system 100, where FIG. 3c shows the endoluminal delivery system 100 having a containment band 104 that envelopes the single delivery capsule 104 of FIG. 3b. In one embodiment of the current invention, the containment band 108 may be made of absorbent material or mesh material, and where any of the surfaces or walls may be made of permeable, semi-permeable, or impermeable material. FIG. 3d depicts another embodiment of the endoluminal delivery system 100 where the containment band 108 has an open span 300 exposing a region of the delivery capsule 104, where the open span 300 may be oriented at any position over the surface of the delivery capsule 104.

Figure 4:
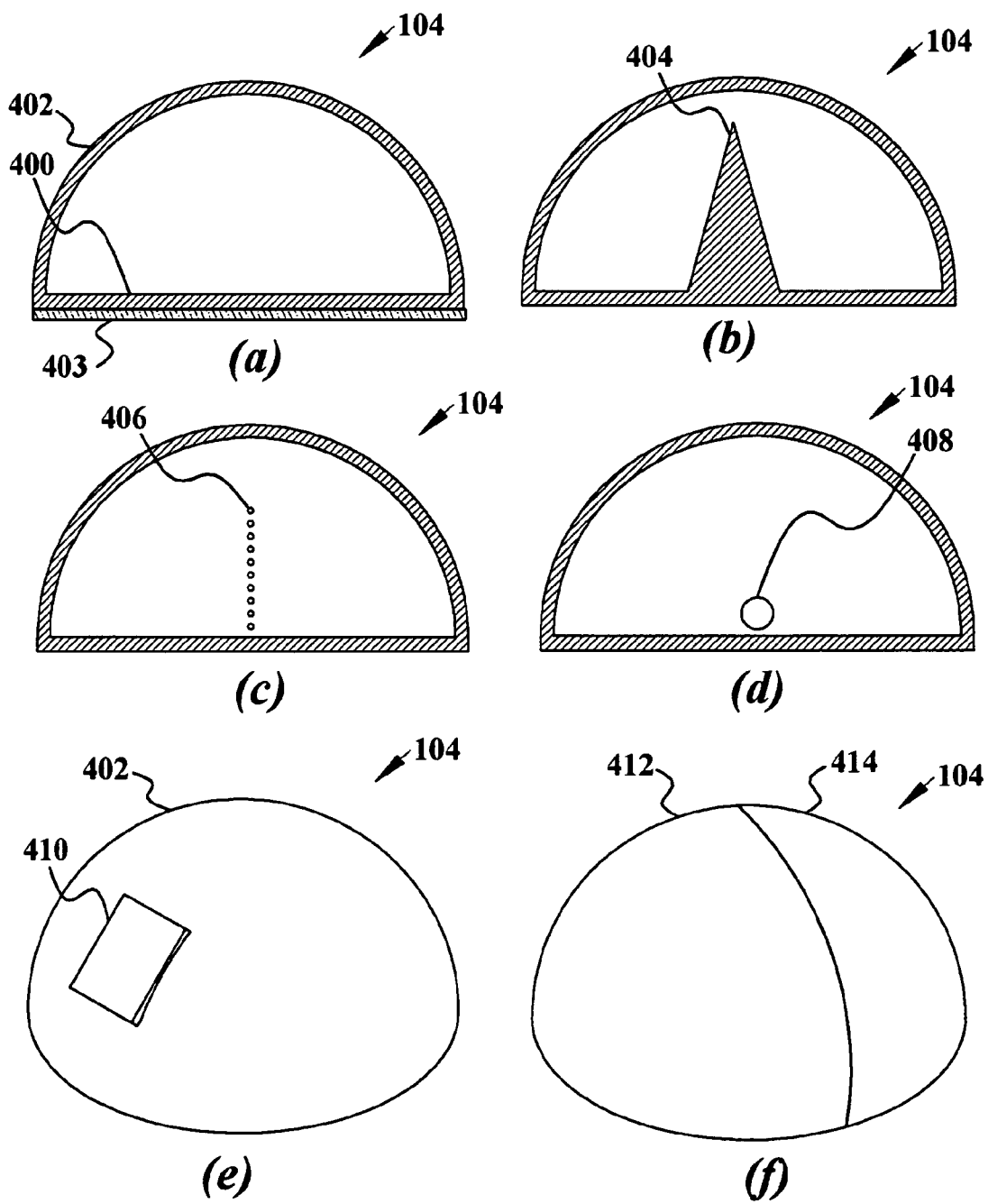
FIGS. 4a-4f depict some embodiments of the delivery capsules according to the present invention.

FIGS. 4a-4f depict some embodiments of the delivery capsules 104 according to the current invention. FIG. 4a depicts a single delivery capsule 104 having a delivery capsule base 400 and a delivery capsule shell 402. In one embodiment of the current invention, the delivery capsule base 400 may be an impermeable barrier, a semi-permeable barrier, or absorbent material. In another embodiment of the current invention, the delivery capsule shell 402 may be an impermeable barrier with a predetermined release pressure, a semi-permeable barrier with a predetermined release pressure, or absorbent material with a predetermined durometer strength. The delivery capsule 104 may further have an impermeable backing barrier 403. FIG. 4b depicts a delivery capsule 104 containing a delivery capsule puncture barb 404, according to one embodiment of the current invention, where the delivery capsule puncture barb 404 is configured to enable reactant 114 delivery according to a predetermined pressure or distortion exerted to the delivery capsule 104. It should be obvious that the delivery capsule puncture barb 404 may be of many shapes and geometries to achieve the desired result. FIG. 4c depicts a delivery capsule 104 according to another embodiment of the invention, having delivery capsule perforations 406 that enable delivery of the reactant 114 according to a desired release direction and delivery pressure. FIG. 4d depicts a delivery capsule 104 according to one embodiment of the current invention, where the delivery capsules 104 have a delivery capsule exit aperture 408 that enable delivery of the reactant 114 according to a desired release direction and delivery pressure. FIG. 4e depicts a delivery capsule 104 according to one embodiment of the current invention, where the delivery capsule 104 has a delivery capsule inelastic element 410 on the delivery capsule 104 to breach the delivery capsule shell 402 when the endoluminal prosthesis 106 expands to the second state. FIG. 4f depicts a delivery capsule 104 according to one embodiment of the current invention, where the delivery capsule 104 has a delivery capsule first volume 412 of the reactant that is released when subject to a first pressure and release a delivery capsule second volume 414 of the reactant when subject to a second pressure.

Figure 5:
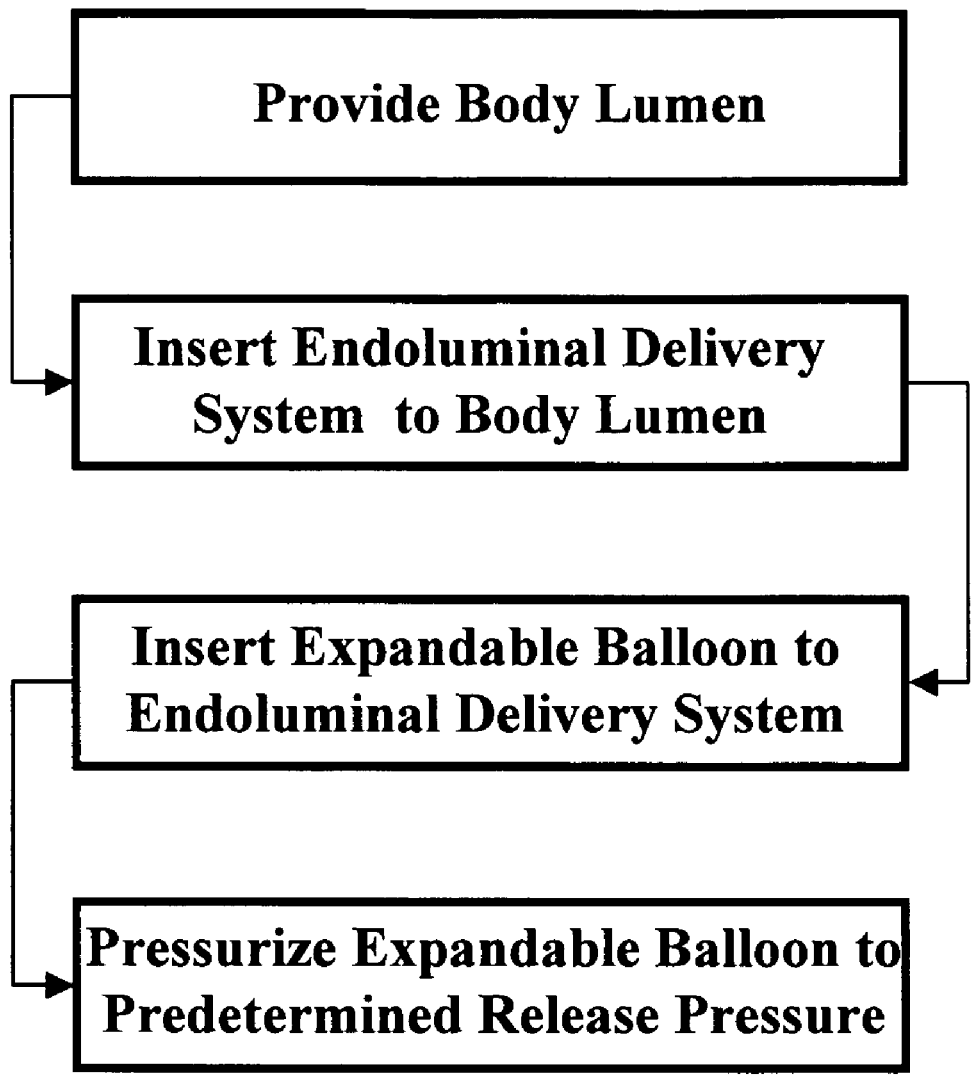
FIG. 5 depicts the steps of using the endoluminal delivery system according to the present invention.

FIG. 5 depicts the steps of using the endoluminal delivery system 100 according to one embodiment of the current invention. A body lumen 102 is provided, and the endoluminal delivery system 100 is inserted to the body lumen 102 with the aid of a guide wire 112, wherein the endoluminal delivery system 100 holds at least one delivery capsule 104 having predetermined release pressure, and having at least one reactant 114 in the delivery capsule 104. An expandable balloon 110 is inserted to the endoluminal delivery system 100. The expandable balloon 110 is pressurized to a predetermined pressure to expand the endoluminal delivery system 100 and induce the predetermined pressure to the delivery capsule 104 against the body lumen 102 to release a predetermined volume of the reactant 114, where the reactant 114 is localized by one or more containment bands 108 to deliver the reactant 114 to the body lumen 102 according to desired positioning and timing.

Figure 6:
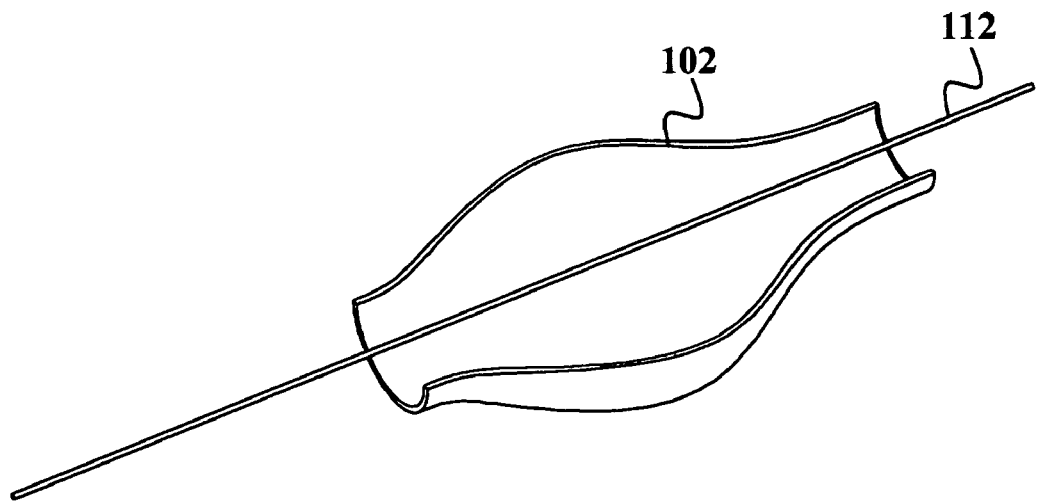
FIGS. 6-13 further depict the use of the endoluminal delivery system according to the present invention.

FIGS. 6 through 13 further depict the use of the endoluminal delivery system 100 according to one embodiment of the current invention. Shown in FIG. 6 is a perspective, partial cutaway view of a body lumen 102 having an inserted guide wire 112.

Figure 7:
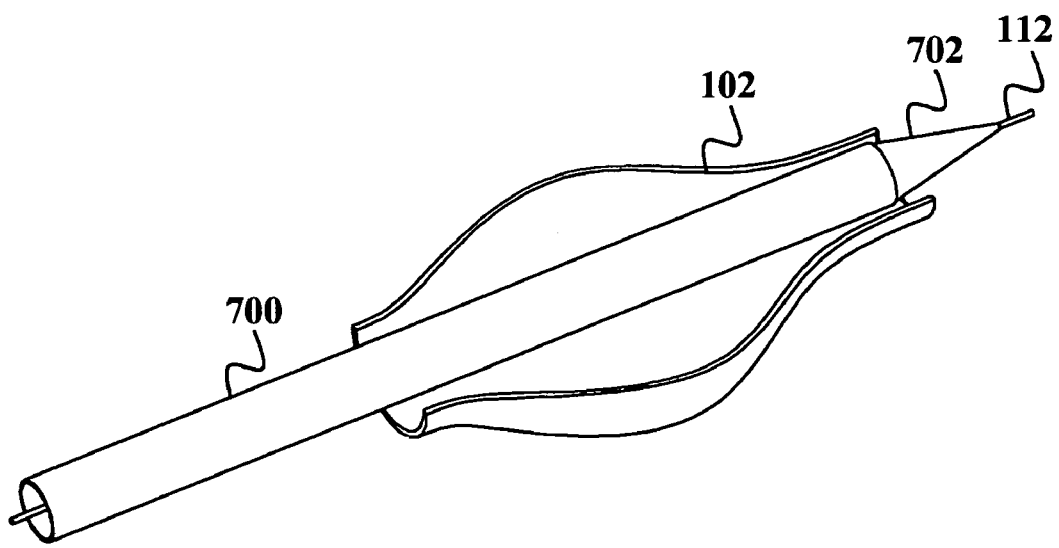

FIG. 7 is a perspective, partial cutaway view of the endoluminal delivery system 100 (not shown) inserted to the body lumen 102 with the aid of the guide wire 112, where depicted is a sheath 700 and an insertion tool 702 encasing the endoluminal delivery system 100.

Figure 8:
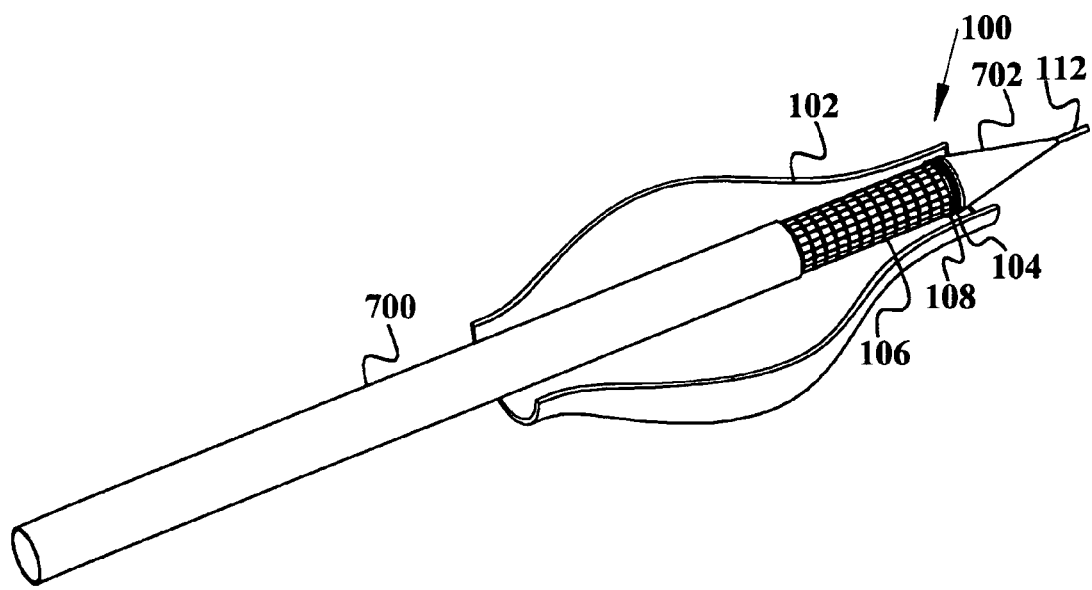

FIG. 8 is a perspective, partial cutaway view of the endoluminal delivery system 100 with the sheath 700 being removed to allow the endoluminal prosthesis 106 to expand to the first state. Shown is the endoluminal delivery system 100 having at least one containment band 108 near a pattern of delivery capsules 104.

Figure 9:
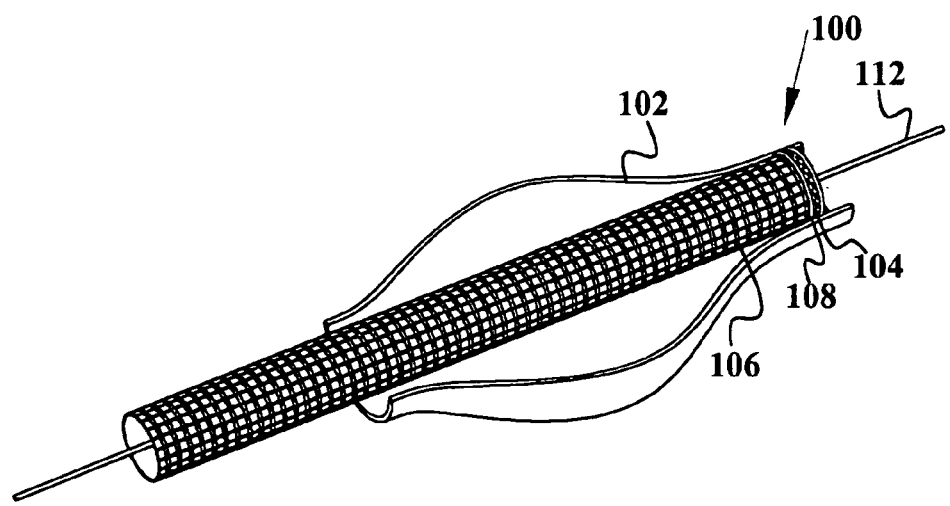

FIG. 9 is a perspective, partial cutaway view of the endoluminal delivery system 100 with the sheath 700 (not shown) completely removed.

Figure 10:
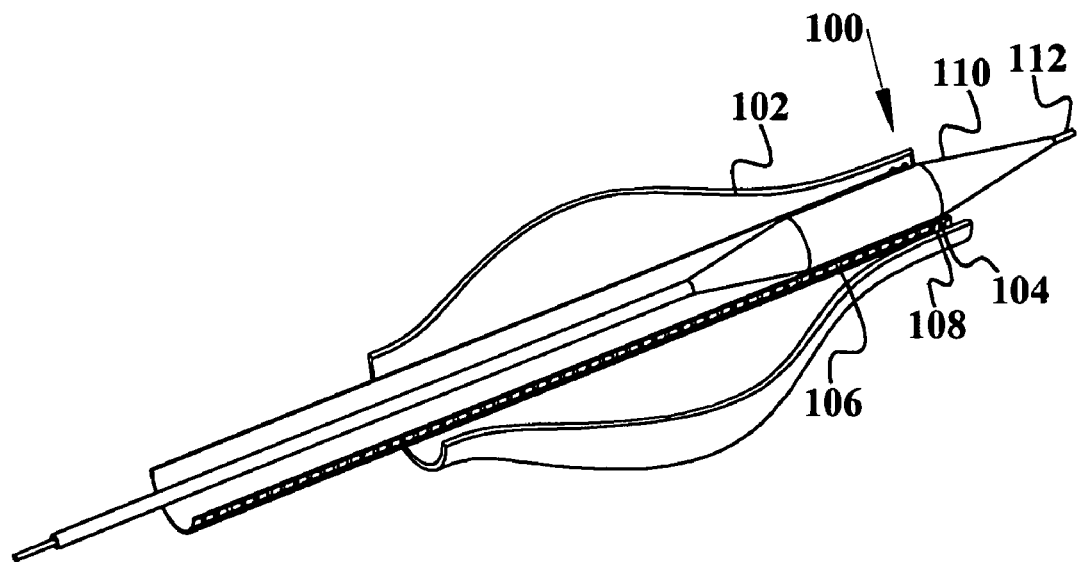
Figure 11:
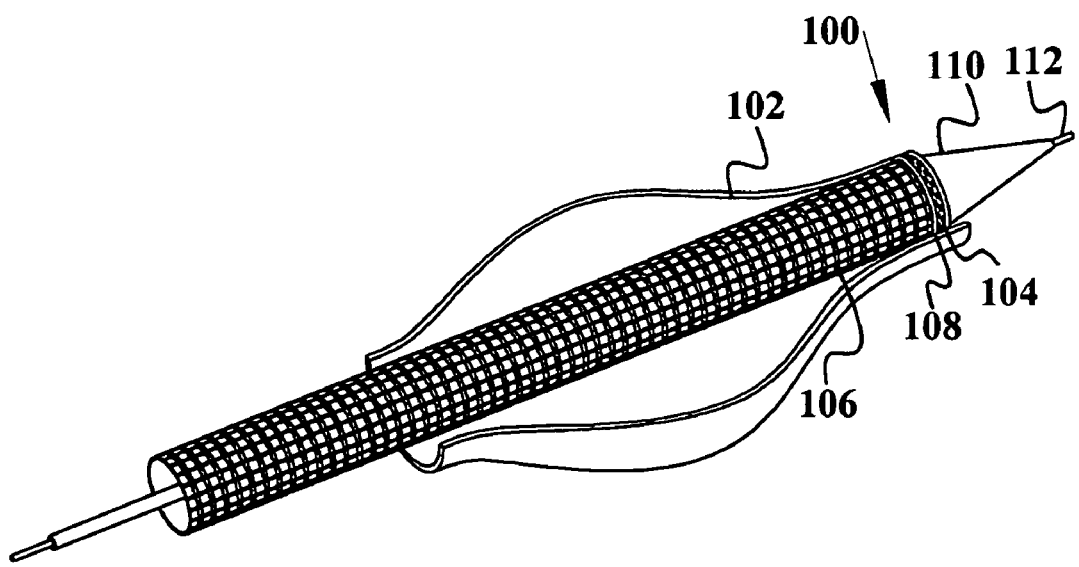

FIGS. 10-11 are perspective, partial cutaway views of the endoluminal delivery system 100 with the balloon inserted, where FIG. 10 shows the endoluminal delivery system 100 cutaway for illustrative purposes with the balloon positioned in the endoluminal prosthesis 106, and FIG. 11 is the same perspective view with the complete endoluminal prosthesis 106 depicted, where the balloon 110 is desirably positioned for inflation. Further depicted in FIG. 11 are the delivery capsules 104 and containment bands 108 in the first unexpanded state.

Figure 12:
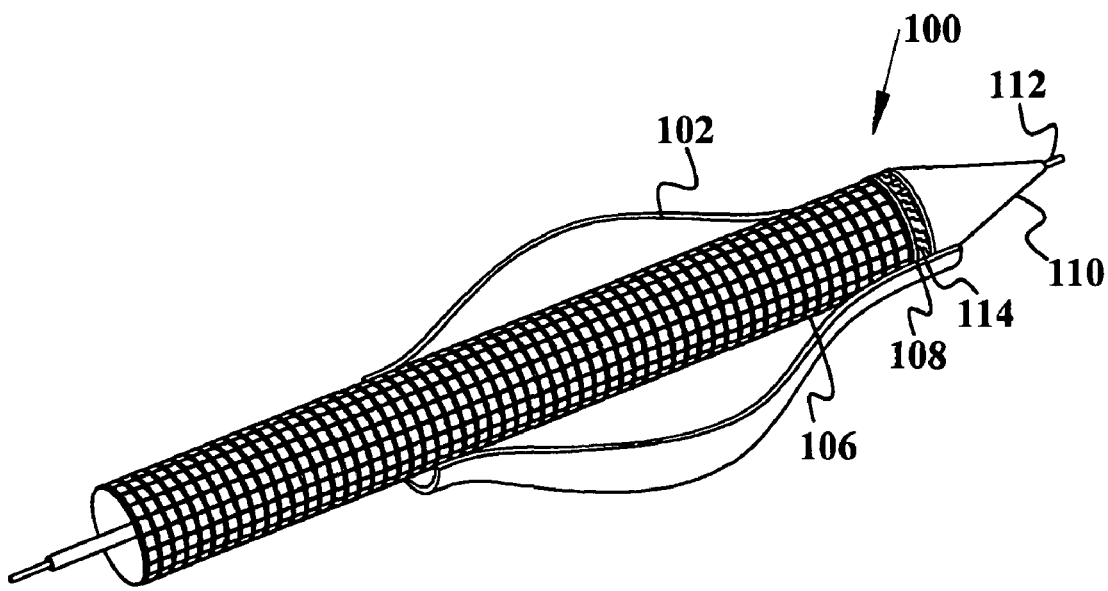

FIG. 12 is a perspective, partial cutaway view of the endoluminal delivery system 100 with the balloon 110 inflated to a predetermined delivery pressure for inducing the delivery capsules 104 (not shown) to press against the body lumen 102 to release the reactants 114, where the reactants 114 are localized by the containment bands 108.

Figure 13:
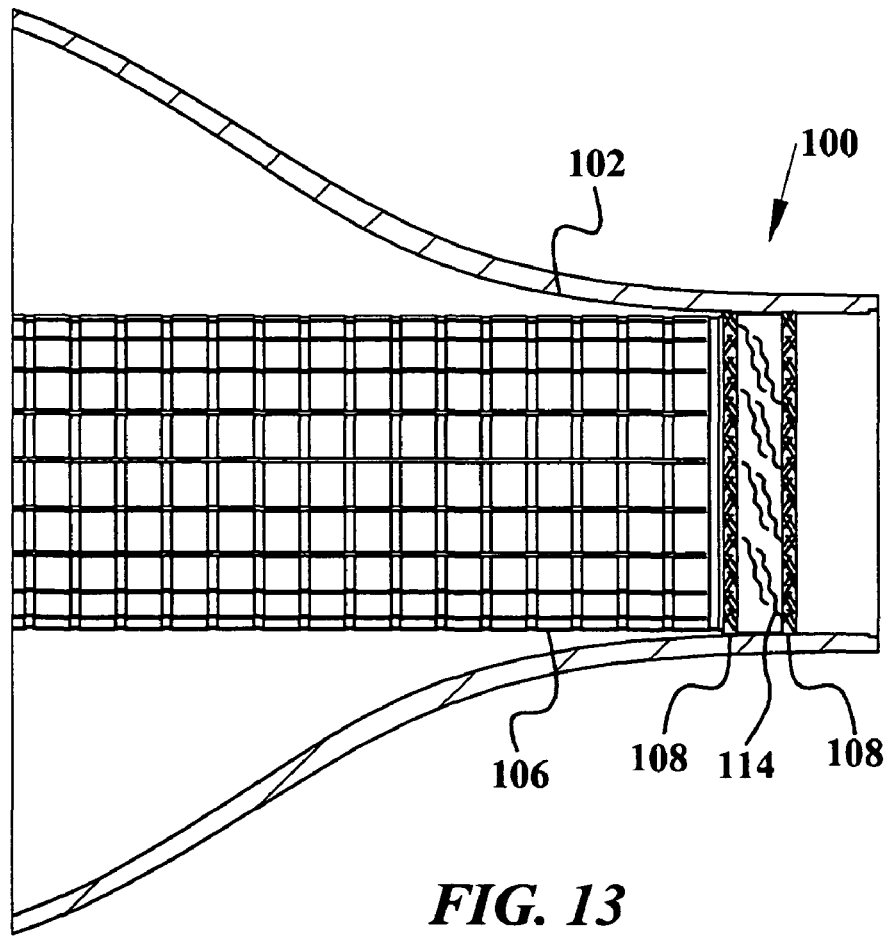

FIG. 13 is a planar partial cutaway view of the endoluminal delivery system 100, where the balloon 110 (not shown) and guide wire 112 (not shown) have been removed and the reactants 114 are delivered while being localized by the containment bands 108. In one embodiment of the invention, the containment bands 108 are made from a mesh material or a sponge material, as depicted in FIG. 13.

In one embodiment of the current invention, the endoluminal prosthesis 106 is a superelastic alloy held by the sheath 700 in the first state, where the step of removing the sheath allows the endoluminal prosthesis 106 to expand to the second state and deliver the reactant to the body lumen 102.

The invention is an endoluminal delivery system 100 having an endoluminal prosthesis 106 inserted to a body lumen 102, at least one delivery capsule 104 having predetermined release pressure is incorporated to the endoluminal prosthesis 106, and at least one reactant in the delivery capsule 104.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example an endoluminal prosthesis in the current invention may be multiple tube structures. In another embodiment of the current invention, the invention could include a single tube structure. The prosthesis could be either a self-expanding or balloon expanding aortic stent graft. The prosthesis could be a percutaneously implanted cardiac valve. This cardiac valve could either be self expanding or balloon expanded. The prosthesis could include an occluder device, such as a cylinder, or capped tube specifically designed to access body lumens, e.g. left atrial appendage. The occluder could be used to block the left atrial appendage, a bronchus or any other body structure. Finally, the prosthesis could enable the connection of 2 lumens to each other.

All such variations are considered to be within the scope and spirit of the present invention as defined by the following claims and their legal equivalents.

What is claimed is:

1. An endoluminal delivery system, comprising:
   a. an endoluminal prosthesis having a first state and a second state, wherein said endoluminal prosthesis is sized to fit through a body lumen in said first state and said second state is expanded relative to said first state;
   b. at least one delivery capsule incorporated to the outer wall of said endoluminal prosthesis; and
   c. at least one reactant in said delivery capsule,
   d. wherein said reactant is released from the delivery capsule when the endoluminal prosthesis is expanded from said first state to said second state, at a pressure releasing reactant between the outer wall of the endoluminal prosthesis and the body lumen as the endoluminal prosthesis contacts the lumen but less than a pressure causing damage to the lumen, so that the reactant remains localized between the endoluminal prosthesis and the body lumen e. at least one containment band incorporated to the outer wall of said endluminal prosthesis and positioned near said delivery capsule to contain said reactant.

2. The endoluminal delivery system of claim 1, wherein said containment band comprises a non-permeable layer on an outer surface, on an inner surface, or an outer surface and an inner surface.

3. The endoluminal delivery system of claim 1, wherein said containment band comprises absorbent material to absorb said reactants and receive tissue growth therein.

4. The endoluminal delivery system of claim 1, wherein said containment band envelopes said delivery capsule.

5. The endoluminal delivery system of claim 1, wherein said containment band has a span exposing a region of said delivery capsule.

6. The endoluminal delivery system of claim 1, wherein said body lumen is selected from the group consisting of cardiac chambers, cardiac valves, arteries, veins, nasal passages, sinuses, trachea, bronchi, oral cavity, esophagus, small intestine, large intestine, anus, ureters, bladder, urethra, vagina, uterus, fallopian tubes, and auditory canals.

7. The endoluminal connector of claim 1, wherein said reactant in said delivery capsules comprise at least an adhesive fluid, or at least a tissue growth promoting fluid, or at least an adhesive fluid and a tissue growth promoting fluid.

8. The endoluminal delivery system of claim 1, wherein said reactant is selected from a group consisting of cyanoacrylates (including 2-octyl cyanoacrylate, n-butyl cyanoacrylate, iso-butyl-cyanoacrylate, methyl-2- or ethyl-2-cyanoacrylate), albumin based sealants, fibrin glues, resorcinol-formaldehyde glues, gelatin-resorcinol-formaldehyde, ultraviolet-light-curable glues, styrene-derivatized (styrenated) gelatin, poly(ethylene glycol) diacrylate (PEGDA), carboxylated camphorquinone in phosphate-buffered saline (PBS), hydrogel sealants—eosin based primer having a copolymer of polyethylene glycol with acrylate end caps with a sealant of polyethylene glycol plus polylactic acid, collagen-based glues, polymethylmethacrylate, vascular endothelial growth factor, fibroblast growth factor, hepatocyte growth factor, connective tissue growth factor, placenta-derived growth factor, angiopoietin-1 or granulocyte-macrophage colony-stimulating factor.

9. The endoluminal delivery system of claim 1, wherein said delivery capsules have a plurality of release pressures.

10. The endoluminal delivery system of claim 9, wherein said delivery capsules are arranged in a pattern according to said release pressures, arranged according to said reactant, or arranged according to said delivery pressures and according to said reactant to release said reactant when subject to said predetermined pressures.

11. The endoluminal delivery system of claim 1, wherein said delivery capsules are arranged in a noninterference pattern, wherein said delivery capsules do not interfere with each other when in said first state or in said second state.

12. The endoluminal delivery system of claim 1, wherein said delivery capsules encapsulate said endoluminal prosthesis.

13. The endoluminal delivery system of claim 1, wherein said delivery capsules contain or appose a delivery capsule puncture barb.

14. The endoluminal delivery system of claim 1, wherein said delivery capsules have an exit aperture.

15. The endoluminal delivery system of claim 1, wherein said delivery capsule further comprise an inelastic element on said delivery capsule to breach said delivery capsule when said endoluminal prosthesis expands to said second state.

16. The endoluminal delivery system of claim 1, wherein said delivery capsules are perforated.

17. The endoluminal delivery system of claim 1, wherein said delivery capsules further comprise an impermeable backing barrier.

18. The endoluminal delivery system of claim 1, wherein said delivery capsules further comprise an absorbent base.

19. The endoluminal delivery system of claim 1, wherein said delivery capsules release a first volume of said reactant when subject to a first pressure and release a second volume of said reactant when subject to a second pressure.

20. The endoluminal delivery system of claim 1, wherein said endoluminal prosthesis is sized to fit through a stent and sized to fit through said body lumen thereby bridging a stent migration gap from said stent to said body lumen.

21. The endoluminal delivery system of claim 1, wherein said endoluminal prosthesis is a shape memory or superelastic alloy held by a sheath in said first state.

22. The endoluminal delivery system of claim 1, wherein said endoluminal prosthesis comprises said delivery capsules juxtaposed in a generally tube shape.

23. An endoluminal delivery system, comprising:
a. an endoluminal prosthesis configured to be inserted into a body lumen;
b. at least one delivery capsule;
c. at least one reactant in said delivery capsule; and
d. at least one containment band on the endoluminal prosthesis at or distal to the delivery capsule for localization of the reactant after release from the delivery capsule;
wherein the reactant is released from the delivery capsule when the endoluminal prosthesis is expanded, at a pressure releasing reactant between the outer wall of the endoluminal prosthesis and the body lumen as the endoluminal prosthesis contacts the lumen but less than a pressure causing damage to the lumen so that the reactant remains localized.

* * * * *